United States Patent [19]

Vanderlaan et al.

[11] Patent Number: Plant 7,298

[45] Date of Patent: Aug. 14, 1990

[54] DIEFFENBACHIA PLANT NAMED TIKI

[75] Inventors: Dan H. Vanderlaan, Lake Worth; Robert Hartman, Lake Placid, both of Fla.

[73] Assignee: Hartman Plant Laboratories, Inc., Sebring, Fla.

[21] Appl. No.: 365,472

[22] Filed: Jun. 13, 1989

[51] Int. Cl.[5] ..... A01H 5/00

[52] U.S. Cl. ..... Plt./89

[58] Field of Search ..... Plt./89

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Dieffenbachia plant named Tiki characterized by its narrow and wavy leaves which have green and gray variegation with white spotting, relatively short habit, and excellent branching.

1 Drawing Sheet

1

The present invention comprises a new and distinct cultivar of Dieffenbachia hybrida known by the cultivar name Tiki.

The new cultivar is a sport found by co-inventors Dan Vanderlaan and Robert Hartman in a population of asexually propagated unnamed *Dieffenbachia memoria* Corsii plants at Vanderlaan's Nursery, Inc., Lake Worth, Fla. The cultivar was a unique combination of the stated traits and characteristics described herein. Asexual propagation by tissue culture was used to increase the number of plants for evaluation and has demonstrated the stability of the combination of characteristics of Tiki from generation to generation.

The following observations, measurements and values describe plants grown in Palmdale, Fla. under greenhouse conditions which closely approximate those generally used in horticultural practice.

The following traits have been repeatedly observed and are determined to be basic characteristics of Tiki, which in combination distinguish Tiki from other Dieffenbachia of the same general type.

1. The green and gray variegated leaves of Tiki are narrower and wavier than plants of *Dieffenbachia memoria* Corsii.

2. Both the upper and lower surfaces of the leaves of Tiki have more white spots than *Dieffenbachia memoria* Corsii.

3. The plant is shorter and branches more than *Dieffenbachia memoria* Corsii.

4. The plants of Tiki maintain more of the juvenile color than *Dieffenbachia memoria* Corsii.

All color references are measured against The Royal Horticultural Society color chart. Colors are approximate as color depends on horticultural practices such as light level and fertilization rate, among others.

The drawing comprises a front perspective color photograph of Tiki, with color being depicted as accurately as possible with illustrations of this type.

The illustrated plant of Tiki is in a six (6) inch pot and approximates a plant 36 to 44 weeks after a plantlet obtained by division is planted and grown under appropriate growing conditions.

Origin: Sport arising from unnamed plants of *Dieffenbachia memoria* Corsii.

Classification: Dieffenbachia, cv. Tiki.

Propagation: Asexual production either by tissue culture or division.

2

Plant: In a 6 inch pot, a plant produced by tissue culture microcutting, after approximately 36–44 weeks and grown under appropriate growing conditions, will be approximately 20 cm. to 28 cm. from the soil surface to the junction of the petioles of the last two (2) unrolled leaves, and approximately 55 cm. to 60 cm. in width. All measurements are based on the above parameters.

Stem:

*Growth pattern.*—The stem is erect in growth and is approximately 2.3 to 2.6 cm. in diameter five (5) cm. above the soil surface. Internode distance will be approximately 1.5 to 1.7 cm. three (3) cm. above the soil.

*Color.*—The stem is 137B.

Petiole: The following information is based on the 4th expanded leaf from the apex.

*Grown pattern.*—The petiole has fleshy edges extending from the midrib that will be referred to as wings. The wings are approximately 11 mm. to 15 mm. wide one-half (½) the distance from the petiole based to the wing tip. The wings extend from the base of the petiole to within approximately 0.8 cm. to 1.2 cm. of the leaf base. The apex of the wings is emarginate. The petiole follows the stem axis but diverges from the axis approximately 8.0 cm. to 9.0 cm. from the leaf base, forming a horizontal distance from the edge of the stem to the leaf base of approximately 3.0 cm. to 4.0 cm.

*Dimensions.*—The petiole is straight from its base to the base of the leaf. The petiole is approximately 8 mm. to 12 mm. in diameter one-half way between the top of the wing and the base of the leaf. The petiole is approximately 11 cm. to 12 cm. in length.

*Color.*—The petiole wings are 137B, 138A in color, and the midrib will be slightly lighter than the petiole.

Leaf:

*Growth pattern.*—The leaf is ovate with an acuminate apex and an obtuse base. The margin is entire. The leaf is asymmetric with the side of the leaf unrolling first having less surface area and fewer undulations on the leaf margin than the side unrolling last. The leaf is highly undulated for a Dieffenbachia. The leaf is oriented parallel to the stem axis at the time of full unrolling, changing to 45° above perpendicular to the stem axis as more leaves unroll above it. The midrib is straight over the length of the leaf. The leaf blade is flat from the midrib to the margin, drooping slightly near the edge.

*Dimensions.*—For the pot size and growing time indicated, the largest leaf is approximately 29 cm. to 33 cm. long and approximately 12 cm. to 15 cm. wide. An average sized leaf is approximately 22 cm. to 26 cm. long and approximately 10 cm. to 12 cm. wide. The leaf is moderately thick.

*Midrib.*—The midrib is thick and prominent.

*Primary veins.*—The primary veins are sunken into the upper surface and protrude out of the underside. The primary veins are the same color as the leaf tissue surrounding them.

*Color and pattern.*—There are numerous areas of the leaf where color is significant. Upper surface: Dark green base color: 139A. Midrib: Greener than 191B, darker than 138B. Gray variegation: 191C, 193A. Spots: 155C. Under surface: Green base color: Greener than 189A. Midrib: 143C. Variegation: 143C. Spots: 157D, 155B.

Axillary breaks: There are approximately 4 to 7 axillary breaks with at least one (1) leaf expanded. Leaves will show color by the first leaf and will have true color and pattern by the second leaf.

Inforescence: Typical of Dieffenbachia and does not have commercial significance.

Roots: Thick white roots with finer laterals.

I claim:

1. A new and distinct cultivar of Dieffenbachia plant named Tiki, as illustrated and described.

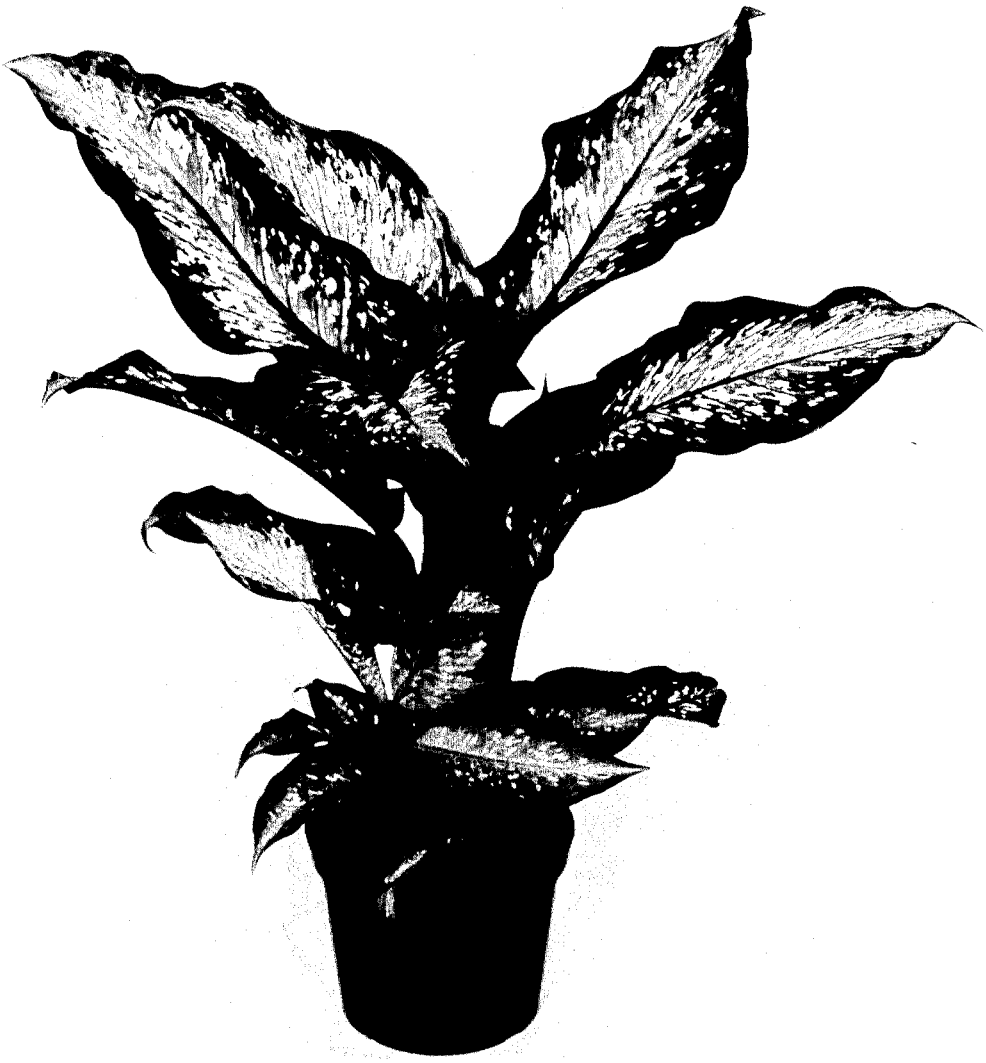

* * * * *